United States Patent [19]

Jaeggi et al.

[11] 4,016,283

[45] Apr. 5, 1977

[54] COMPOSITION AND METHOD FOR TREATMENT OF HEART AND CIRCULATORY AILMENTS

[75] Inventors: Knut A. Jaeggi, Basel; Franz Ostermayer, Riehen; Herbert Schröter, Fullinsdorf, all of Switzerland

[73] Assignee: Ciba-Geigy Corporation, Ardsley, N.Y.

[22] Filed: Nov. 24, 1975

[21] Appl. No.: 634,809

Related U.S. Application Data

[62] Division of Ser. No. 447,118, Feb. 28, 1974, Pat. No. 3,984,436.

[30] Foreign Application Priority Data

Mar. 9, 1973 Switzerland .................... 3518/75

[52] U.S. Cl. .............................. 424/274; 424/246; 424/248.58; 424/250; 424/267
[51] Int. Cl.² ........................................ A61K 31/40
[58] Field of Search .......... 424/246, 248, 250, 267, 424/274; 260/293.7, 307 C, 326.5 L

[56] References Cited

UNITED STATES PATENTS 3,328,417  6/1967  McLoughlin .................... 260/307

*Primary Examiner*—Albert T. Meyers
*Assistant Examiner*—A. P. Fagelson
*Attorney, Agent, or Firm*—Joseph G. Kolodny; John J. Maitner; Theodore O. Groeger

[57]  ABSTRACT

Pyrrolyl compounds of the formula I

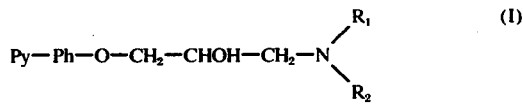

wherein Py is optionally lower-alkylated 1-pyrrolyl, Ph is phenylene, $R_1$ is hydrogen or lower alkyl and $R_2$ is hydrogen, lower alkyl, aryl-lower alkyl or optionally functionally modified carboxy-lower alkyl or $R_1$ and $R_2$ together are loweralkylene, oxa-lower alkylene, thia-lower alkylene or aza-lower alkylene, their antipodes and salts, which are valuable blockers of adrenergic β-receptors and useful in the treatment of heart and circulatory ailments.

2 Claims, No Drawings

COMPOSITION AND METHOD FOR TREATMENT OF HEART AND CIRCULATORY AILMENTS

This is a division of application Ser. No. 447,118 filed Feb. 28, 1974, now U.S. Pat. No. 3,984,436.

The invention relates to new pyrrolyl compounds of the formula I

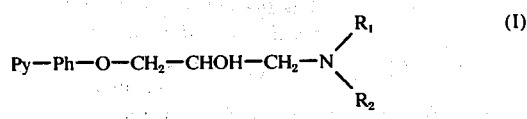

wherein Py is optionally lower alkylated 1-pyrrolyl, Ph is phenylene, $R_1$ is hydrogen or lower alkyl and $R_2$ is hydrogen, lower alkyl, aryl-lower alkyl or optionally functionally modified carboxy-lower alkyl or $R_1$ and $R_2$ together are lower alkylene, oxa-lower alkylene, thia-lower alkylene or aza-lower alkylene, and to processes for their manufacture.

In the preceeding and following text, a lower radical is in particular understood as a radical with up to 7 C atoms, above all with up to 4 C atoms.

Lower alkyl $R_1$ and $R_2$, and lower alkyl as a substituent of pyrrolyl Py, preferably has up to 7 C atoms, above all up to 4 C atoms, such as straight or branched butyl, pentyl, hexyl or heptyl bonded in any desired position, but especially n-propyl, ethyl and above all methyl, isopropyl and tert.-butyl and, in the case of a substituent of pyrrolyl Py, above all methyl.

Lower alkyl substituents are in particular bonded in the 2- and/or 5-position to a 1-pyrrolyl radical.

Phenylene Ph is meta-phenylene and especially ortho-phenylene or para-phenylene.

Aryl-lower alkyl $R_2$ preferably has up to 12 C atoms, above all up to 10 C atoms, and is unbranched or, preferably, branched in the lower alkyl part, and in particular branched at the α-C atom of the lower alkyl part. The aryl part is, in particular, a phenyl radical which is optionally polysubstituted or, in particular, monosubstituted by lower alkyl, such as the lower alkyl indicated above, lower alkoxy, halogen or trifluoromethyl but is preferably unsubstituted. Examples of aryl-lower alkyl $R_2$ are 1-methyl-3-phenyl-propyl and especially 1-methyl-2-phenylethyl.

Lower alkoxy preferably has up to 7 C atoms, above all up to 4 C atoms, and is therefore preferably straight or branched butoxy, pentyloxy, hexyloxy or heptyloxy or above all iso- or n-propoxy, ethoxy or, especially, methoxy.

Halogen is, for example, bromine and especially chlorine.

Optionally functionally modified carboxy-lower alkyl $R_2$ preferably has up to 7 C atoms, above all up to 4 C atoms, in the lower alkyl part and is unbranched or preferably branched, in particular branched at the α-C atom. Optionally functionally modified carboxy-lower alkyl is thus preferably carboxymethyl, 2-(2-carboxy)-propyl, 2-(4-carboxyl)-butyl or especially 2-carboxyethyl or above all 2-(3-carboxy)-propyl functionally modified at the carboxyl group. The optionally functionally modified carboxyl group is, for example, free, esterified or amidised carboxyl or nitrile.

Esterified carboxyl is, for example, carboxyl esterified with an aliphatic alcohol. Aliphatic alcohols are those in which the hydroxyl group is bonded to a C atom which is not a member of an aromatic system.

Suitable aliphatic alcohols are, for example, cycloalkanols, such as those with 3-7, especially 5-7, ring members, for example cyclopropanol, cyclopentanol, cyclohexanol and cycloheptanol, cycloalkyl-lower alkanols, which contain, for example, the above cycloalkyl parts, such as cyclopentyl-methanol, cyclohexyl-methanol, 2-cyclohexyl-ethanol and cycloheptyl-methanol, phenyl-lower alkanols, such as 2-phenylethanol and benzyl alcohol, wherein phenyl radicals can also be substituted by halogen, lower alkyl and/or lower alkoxy, such as those mentioned above, and especially lower alkanols, such as n-propanol, iso-propanol, straightchain or branched butanol, pentanol, hexanol or heptanol, and especially methanol or ethanol. Thus, esterified carboxyl is, above all, methoxycarbonyl or ethoxycarbonyl.

Amidised carboxyl is substituted or unsubstituted carbamoyl. Substituted carbamoyl has, for example, the formula $-Co-NR_3R_4$, wherein $R_3$ is hydrogen or lower alkyl, $R_4$ is lower alkyl or $R_3$ and $R_4$ together are lower alkylene, oxa-lower alkylene, thia-lower alkylene or aza-lower alkylene. Lower alkyl in particular has the abovementioned meaning.

Lower alkylene $R_3 + R_4$, and $R_1 + R_2$, is branched or, in particular, straight-chain or lower alkylene with, in particular, 2–7, above all 4–6, C atoms in the alkylene chain, and in particular represents, together with the N atom to which the lower alkylene is bonded, pyrrolidino or piperidino.

Oxa-lower alkylene $R_3 + R_4$, and $R_1 + R_2$, is branched or, in particular, straight-chain oxa-lower alkylene with, in particular, 4 to 5 C atoms in the oxa-alkylene chain, and in particular represents, together with the N atom to which the oxa-lower alkylene is bonded, morpholino.

Thia-lower alkylene $R_3 + R_4$, and $R_1 + R_2$, is branched or, in particular, straight-chain thia-lower alkylene with, in particular, 4 or 5 C atoms in the thia-alkylene chain and in particular represents, together with the N atom to which the thia-lower alkylene is bonded, thiomorpholino or 2,6-dimethylthiomorpholino.

Aza-lower alkylene $R_3 + R_4$, and $R_1 + R_2$, is branched or straight-chain aza-lower alkylene with, in particular, 2–6, all above 4–6, C atoms in the aza-alkylene chain, and in particular represents, together with the N atom to which the aza-lower alkylene is bonded, piperazino, N'-methylpiperazino or N'-(β-hydroxyethyl)-piperazino.

The new compounds possess valuable pharmacological properties. Thus they show an excitation-inhibiting action, as can be demonstrated on determining the pargyline-reserpine antagonism on intraperitoneal administration of doses of about 0.4 to 10 mg/kg to mice. The new compounds therefore are useful for the treatment of states of excitation. They block cardiac β-receptors, as is evident from the determination of the antagonism to tachycardia when administered intravenously in doses of 0.01 to 1 mg/kg to narcotised cats that have been treated intravenously with 0.5 μg/kg of d/l-isoproterenol sulphate. They also block vascular β-receptors, as is manifest from the determination of vasodilation when administered intravenously in doses of 0.01 to 1 mg/kg to narcotised cats that have been treated i.v. with 0.5 μg/kg of d/l-isoproterenol sulphate, and they also block cardiac β-receptors, as is clear from the determination of tachycardia when administered in a concentration of 0.01 to 1 μg/ml after treating isolated guinea pig hearts in vitro with 0.005 μg/ml of d/1-isoproterenol sulphate. The new compounds therefore are useful as blockers of adrenergic β-receptors in the treatment of heart and circulatory ailments, e.g. arrhythmic disturbances, angina pectoris and hypertension. They can, however, also be used as valuable intermediate products for the manufacture of other useful materials, especially pharmaceutically active compounds.

Compounds to be singled out are compounds Ia of the formula I, wherein Py is optionally mono- or di-lower alkylated 1-pyrrolyl, Ph is phenylene, $R_1$ is hydrogen or lower alkyl and $R_2$ is hydrogen, lower alkyl, aryl-lower alkyl, carbamoyl-lower alkyl or cyano-lower alkyl or $R_1$ and $R_2$ together are lower alkylene, oxa-alkylene, thia-lower alkylene or aza-lower alkylene.

Compounds to be singled out particularly are compounds Ib of the formula I, wherein Py is optionally mono or di-lower alkylated 1-pyrrolyl, Ph is ortho- or para-phenylene, $R_1$ is hydrogen or lower alkyl and $R_2$ is hydrogen, lower alkyl, phenyl-lower alkyl, carbamoyl-lower alkyl or cyano-lower alkyl or $R_1$ and $R_2$ together are lower alkylene, oxa-lower alkylene, thia-lower alkylene or aza-lower alkylene.

Compounds which are particularly suitable are compounds Ic of the formula I, wherein Py is 1-pyrrolyl, methyl-1-pyrrolyl or dimethyl-1-pyrrolyl, Ph is ortho- or para-phenylene, $R_1$ is hydrogen, methyl or ethyl and $R_2$ is methyl, ethyl, isopropyl, tert.-butyl, α-methylphenethyl, carbamoyl-lower alkyl with up to 5 C atoms or cyano-lower alkyl with up to 5 C atoms, or $R_1$ and $R_2$ together with the N atom to which they are bonded are pyrrolidino, piperidino, morpholino, thiomorpholino, piperazino, N'-methylpiperazino or N'-(β-hydroxyethyl)-piperazino.

Compounds to be singled out very particularly are compounds $I_d$ of the formula I, wherein Py is 1-pyrrolyl or mono- or di-lower alkylated 1-pyrrolyl, Ph is ortho- or para-phenylene, $R_1$ is hydrogen or lower alkyl and $R_2$ is lower alkyl or $R_1$ and $R_2$ together are lower alkylene, oxa-lower alkylene, thia-lower alkylene or aza-lower alkylene and, in particular, Py is 1-pyrrolyl or 2,5-dimethyl-1-pyrrolyl, Ph is ortho- or para-phenylene, $R_1$ is hydrogen, $R_2$ is iso-propyl or tert.-butyl or $R_1$ and $R_2$ together with the N atom to which they are bonded are morpholino, and above all the compounds mentioned in the examples.

The new compounds are obtained according to methods which are in themselves known.

Thus, for example, a possible procedure is to react a compound of the formula II

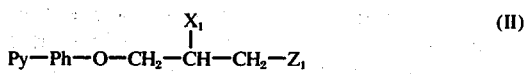

with a compound of the formula III $$Z_2-R_1 \text{ or } Z_2-R_2 \qquad (III)$$

wherein Py, Ph, $R_1$ and $R_2$ have the above meanings, one of the radicals $Z_1$ and $Z_2$ is -NH-$R_2$ or -NH-$R_1$ and the other is reactively esterified hydroxyl and $X_1$ is hydroxyl or, if $Z_2$ is —NH—$R_2$ or —NH—$R_1$, $Z_1$ together with $X_1$ is epoxy. However, $Z_1$ must not denote $NH_2$.

A reactive esterified hydroxyl group is, in particular, a hydroxyl group esterified by a strong inorganic or organic acid, above all a hydrogen halide acid, such as hydrochloric acid, hydrobromic acid or hydriodic acid, or sulphuric acid, or a strong organic sulphonic acid, such as a strong aromatic sulphonic acid, for example benzenesulphonic acid, p-bromobenzenesulphonic acid or p-toluenesulphonic acid. Thus, $Z_1$ or $Z_2$ in particular represents chlorine, bromine or iodine.

This reaction is carried out in the usual manner. If a reactive ester is used as the starting material, the reaction is preferably carried out in the presence of a basic condensation agent and/or with an excess of amine. Examples of suitable basic condensation agents are alkali metal hydroxides, such as sodium hydroxide or potassium hydroxide, alkali metal carbonates, such as potasssium carbonate, and alkali metal alcoholates, such as sodium methylate, potassium ethylate and potassium tertiary butylate.

A further possible procedure is to react a compound of the formula IV

with a compound of the formula V

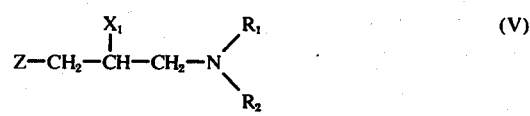

wherein Py, Ph, $R_1$ and $R_2$ have the above meanings, Z is a reactive esterified hydroxyl group and $X_1$ is hydroxyl, or Z and $X_1$ together form an epoxy group.

A reactive esterified hydroxyl group is, in particular, a hydroxyl group esterified by a strong inorganic or organic acid, above all a hydrogen halide acid, such as hydrochloric acid, hydrobromic acid or hydriodic acid, or sulphuric acid, or a strong organic sulphonic acid, such as a strong aromatic sulphonic acid, for example benzenesulphonic acid, p-bromobenzenesulphonic acid or p-toluenesulphonic acid. Thus, Z in particular represents chlorine, bromine or iodine.

This reaction is carried out in the usual manner. If reactive esters are used as the starting material, the compound of the formula IV can preferably be used in the form of its metal phenolate, such as alkali metal phenolate, for example sodium phenolate, or the reaction is carried out in the presence of an acid-binding agent, especially a condensation agent which can form a salt with the compound of the formula IV, such as an alkali metal alcoholate, hydroxide or carbonate.

A further possible procedure is that in the compound of the formula I, wherein Py, Ph, $R_1$ and $R_2$ have the above meanings and which optionally possesses a removable radical on the nitrogen atom of the —$NR_1R_2$ amino group and/or on the 2-hydroxyl group, this radical or these radicals is or are removed.

Such removable radicals are, in particular, radicals removable by solvolysis, such as radicals removable by hydrolysis or ammonolysis or by reduction.

Examples of radicals which are removed by hydrolysis are acyl radicals, such as optionally functionally modified carboxyl groups, for example oxycarbonyl radicals, such as alkoxycarbonyl radicals, for example the tert.-butoxycarbonyl radical or the ethoxycarbonyl radical, aralkoxycarbonyl radicals, such as phenyl-lower alkoxycarbonyl radicals, for example a carbobenzoxy radical, halogenocarbonyl radicals, for example the chlorocarbonyl radical, and also arysulphonyl radicals, such as toluenesulphonyl or bromobenzenesulphonyl radicals, and optionally halogenated, such as fluorinated, lower alkanoyl radicals, for example the formyl, acetyl or trifluoroacetyl radical, or aroyl radicals which are optionally substituted like the radical Ph, for example the benzoyl radical, or nitrile groups or silyl radicals, such as the trimethylsilyl radical.

Possible radicals, removable by hydrolysis, on the hydroxyl group are, amongst those mentioned, in particular oxycarbonyl radicals, lower alkanoyl radicals and benzoyl radicals.

Compounds with radicals removable by ammonolysis or especially by hydrolysis are, in particular, compounds of the formula VI

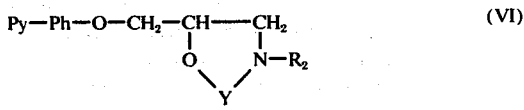

wherein Py, Ph and $R_2$ have the above meanings and Y represents a carbonyl or thiocarbonyl radical or, in particular, a divalent radical of an aldehyde or ketone formally obtainable by replacement of the oxo group.

Ketones are, for example, di-lower alkylketones, such as methyl ethyl ketone or acetone, or lower alkyl aryl ketones, such as phenyl methyl ketone. Aldehydes are, for example, lower alkanals, such as those with, in particular, up to 7 C atoms, such as acetaldehyde or above all formaldehyde, or aryl-lower alkanals, such as phenyl-lower alkanals, for example benzaldehyde.

The hydrolysis is carried out in the usual manner, for example in the presence of hydrolysing agents, for example in the presence of acid agents, such as, for example, of an aqueous mineral acid, such as sulphuric acid or a hydrogen halide acid, or of an organic acid, for example a suitable carboxylic acid, such as an α-halogenoalkanecarboxylic acid, for example trifluoroacetic acid or chloroacetic acid, an organic sulphonic acid, for example benzenesulphonic acid or toluenesulphonic acid, or of acid ion exchangers, or in the presence of basic agents, for example alkali metal hydroxides, such as sodium hydroxide. Oxycarbonyl radicals, arysulphonyl radicals and nitrile groups can advantageously be removed by acid agents, such as by a hydrogen halide acid, especially hydrobromic acid. The removal by means of aqueous hydrobromic acid, optionally mixed with acetic acid is, for example, particularly suitable. Nitrile groups are in particular removed by hydrobromic acid at an elevated temperature, such as in boiling hydrobromic acid, by the cyanogen bromide method (v. Braun). Further, for example, a tert.-butoxycarbonyl radical can be split off under anhydrous conditions by treatment with a suitable acid, such as trifluoroacetic acid. In the hydrolysis of compounds of the formula VI, in particular, acid agents are suitably used.

However, care must be taken in the hydrolysis that other substituents are not attacked. Thus, the hydrolysis is advantageously carried out under gentle conditions, for example by starting from starting compounds which are easily hydrolysable in the desired manner, for example from those of the formula VI, wherein Y denotes a divalent radical of an aldehyde or of a ketone, and preferably using short reaction times and/or mild hydrolysing agents. Prolonged heating in an acid medium can reduce the yields.

Radicals removable by ammonolysis are, in particular, functionally modified carboxyl radicals, above all esterified carboxyl radicals, such as alkoxycarbonyl radicals, or acid anhydride radicals, such as halogenocarbonyl radicals, for example the chlorocarbonyl radical. Further starting materials containing radicals removable by ammonolysis are also compounds of the formula VI, wherein Py, Ph and $R_2$ have the indicated meanings and Y represents the carbonyl or thiocarbonyl radical.

The ammonolysis can be carried out in the usual manner, for example by means of an amine which carries at least one hydrogen atom on the nitrogen atom, such as a mono- or di-lower alkylamine, for example methylamine or dimethylamine, or especially by means of ammonia, preferably at elevated temperature. Instead of ammonia it is also possible to use an agent which gives off ammonia, such as hexamethylenetetramine.

Radicals removable by reduction are, for example, α-arylalkyl radicals, such as benzyl radicals, or α-aralkoxycarbonyl radicals, such as benzyloxycarbonyl radicals, which can be split off in the usual manner by hydrogenolysis, especially by catalytically activated hydrogen, such as by hydrogen in the presence of a hydrogenation catalyst, for example platinum, palladium or Raney nickel. Examples of further radicals which can be split off by hydrogenolysis are 2-halogenoalkoxycarbonyl radicals, such as the 2,2,2-trichloroethoxy-carbonyl radical or the 2-iodoethoxy-carbonyl or 2,2,2-tribromoethoxy-carbonyl radical, which can be split off in the usual manner, especially by metallic reduction (so-called nascent hydrogen). Nascent hydrogen can be obtained by the action of metal or metal alloys, such as amalgams, on agents which provide hydrogen, such as carboxylic acids, alcohols or water, and in particular, zinc or zinc alloys together with acetic acid can be used. The hydrogenolysis of 2-halogeno-alkoxycarbonyl radicals can also be effected by chromium-(II) compounds, such as chromium-(II) chloride or chromium-(II) acetate. A radical removable by reduction can also be an arylsulphonyl group such as the toluenesulphonyl group, which can be removed, in particular removed from a N atom, in the usual manner by reduction with nascent hydrogen, for example by means of an alkali metal, such as lithium or sodium, in liquid ammonia.

A further possible procedure is to reduce a Schiff's base corresponding to the formula I, wherein the N atom is doubly bonded to a substituent $R_1$ or $R_2$ or to the propoxy part and optionally carries a positive charge, or a tautomer or hydrate thereof.

For example, a possible procedure is to reduce a Schiff's base of the formula VIIa, VIIb, VIIIa or VIIIb

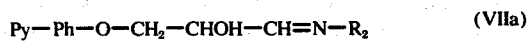

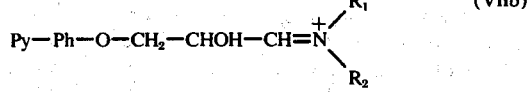

-continued

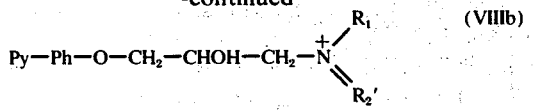

or a ring tautomer of the formula IXa or IXb corresponding to the formula VIIIa or VIIIb

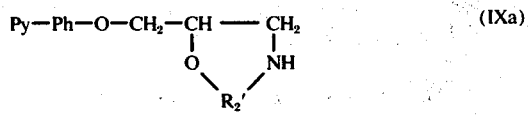

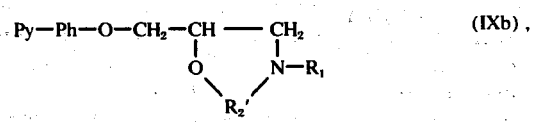

wherein Py, Ph, $R_1$ and $R_2$ have the above meanings and $R'_2H$ is the same as $R_2$, it also being possible for compounds of the formulae VIII and IX to be present alongside one another.

The reduction can be carried out in the usual manner, for example by means of hydrogen in the presence of a hydrogenation catalyst, such as nickel, platinum or palladium, for example Raney nickel, platinum black or palladium on active charcoal. Optionally, the hydrogen uptake is followed volumetrically and the hydrogenation is discontinued after the calculated amount of hydrogen has been taken up. The reduction can, however, also be effected with, for example, formic acid or a hydride reducing agent, such as with hydrides, for example simple or complex hydrides, such as with a borane, for example diborane, or with a complex di-light metal hydride, for example with an alkali metal-aluminium hydride, such as lithium aluminium hydride, sodium aluminum hydride or sodium tris-(2-dimethylaminoethoxy)-aluminum hydride or sodium cyanoborohydride.

A further possible procedure is to react a compound of the formula X

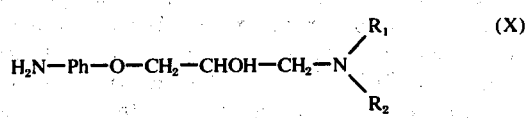

with a γ-oxo-lower alkanone or a tautomer or functional derivative thereof.

A γ-oxo-lower alkanone, a tautomer or a functional derivative can be in the monomeric or in the polymeric form. A functional derivative can be open-chain or cyclic, such as an open-chain or cyclic acetal, ketal or acylal or an open-chain or cyclic α-halogeno-ether, enol-ether or enol-ester. A γ-oxo-lower alkanone can also be present as a mixture with its tautomer and/or its functional derivatives. As examples of suitable γ-oxo-lower alkanones there may be mentioned: Succinaldehyde, 2-methyl-succinaldehyde, 2,3-dimethyl-succinaldehyde, levulinaldehyde, 4-oxo-hexaldehyde and 2,5-hexanedione. As examples of suitable derivatives of γ-oxo-lower alkanones there may be mentioned: Monomeric acetals of succinaldehyde, such as succinaldehyde-monodiethylacetal, -bis-dimethylacetal, and -bis-diethylacetal, acylals such as succinaldehyde-1,1-diacetate (4,4-diacetoxybutyraldehyde), enol-ethers such as 1,4-diphenoxy-butadiene and enol-esters such as 1,4-diacetoxy-butadiene. Further suitable compounds are, for example, derivatives of tetrahydrofurane, which react, for example, like the acetals or acylals of succinaldehyde or like open-chain α-halogenoethers. Such compounds are, for example, optionally lower alkyl-substituted 2,5-dialkoxytetrahydrofuranes and related compounds, such as 2,5-dimethoxy-, 2,5-diethoxy-, 2,5-dipropoxy-, 2,5-dibutoxy-, 2,5-bisallyloxy-, 2,5-bis-(2-chloroethoxy)-, 2,5-diphenoxy- and 2,5-bis-(3,4-xylyloxy)-tetrahydrofurane, 2-methyl-2,5-dimethoxy-tetrahydrofurane and 3-methyl-2,5-dimethoxy-tetrahydrofurane, and also 2,5-diacyloxy-tetrahydrofuranes, such as 2,5-diacetoxy-tetrahydrofurane, as well as 2,5-dihalogeno-tetrahydrofuranes, such as 2,5-dichloro-tetrahydrofurane and 2,5-dibromotetrahydrofurane, and also compounds which are simultaneously to be classified under two types, such as 2-chloro-5-(2-chloroethoxy)-tetrahydrofurane and 2-allyloxy-5-chloro-tetrahydrofurane.

Polymeric compounds of the abovementioned nature are obtained, for example, when polymeric aldehydes, such as polymeric succinaldehyde, are reacted with amounts of acetalising or acylating materials, or mixtures of materials, which are less than equivalent to the succinaldehyde units present.

The reaction of a compound X with a γ-oxo-lower alkanone, a tautomer thereof or a functional derivative thereof, can be carried out in the usual manner, especially warm, such as at about +30° to +140° and in the presence or absence of a diluent and/or condensation agent.

Suitable media for the reaction according to the invention are, when using a free γ-oxo-lower alkanone, any solvent in which this compound is soluble, for example lower alkanols, such as methanol and ethanol, or lower alkanecarboxylic acids, such as acetic acid. Acetals and acylals of the γ-oxo-lower alkanones, as well as cyclic acetal-like derivatives are advantageously reacted in lower alkanecarboxylic acids, such as acetic acid, as the solvent and condensation agent, or in the presence of catalytical amounts of an acid condensation agent, such as p-toluene sulphonic acid, in the presence or absence of an inert organic solvent or diluent, such as, for example, benzene, toluene, o-dichlorobenzene or acetonitrile. The reaction of α-halogenoethers is carried out, for example, in inert organic solvents, such as halogeno-lower alkanes, for example chloroform or the abovementioned solvents. the reaction temperature is preferably between room temperature and the boiling point of the solvent or diluent used, for example +25° to +140°, the lowest range in particular being relevant to the last-mentioned halogen compounds.

In resulting compounds, it is possible, within the scope of the definition of the end products, to modify, introduce or remove substituents in the usual manner, or to convert resulting compounds in the usual manner into other end products.

Thus, it is possible, in resulting compounds, to hydrolyse functionally modified carboxyl groups, as a constituent of $R_2$, to free carboxyl groups in the usual manner, preferably in the presence of a strong base, such as a strong organic or, above all, inorganic base, preferably a metal base, for example an alkaline earth metal or alkali metal carbonate or, above all, hydroxide, for example calcium hydroxide, sodium hydroxide or potassium hydroxide, or in the presence of a strong acid, for example a strong mineral acid, especially a hydrogen halide acid, for example hydrochloric acid or above all hydrobromic acid, or sulphuric acid. If desired, oxidising agents such as nitrous acid, can be added when hydrolysing the carbamoyl group.

The nitrile group as a constituent of $R_2$ can also be hydrolysed to the carbamoyl group in the usual manner, for example as described above for the hydrolysis to the free carboxyl group. Equally, it is also possible to convert the carbamoyl group into the nitrile group by dehydration in the usual manner, for example by heating and/or by the action of dehydrating agents.

Free carboxyl groups as a constituent of $R_2$ can be esterified in the usual manner, for example by reaction with a corresponding alcohol, preferably in the presence of an acid, such as a mineral acid, for example sulphuric acid or hydrochloric acid, or in the presence of a water-binding agent, such as dicyclohexylcarbodiimide, or by reaction with an appropriate diazo compound, for example a diazoalkane. The esterification can also be carried out by reaction of a salt, preferably an alkali metal salt, of the acid with a reactively esterified alcohol, for example a halide, such as the chloride, of the corresponding alcohol.

Free carboxyl groups can also be converted into amidised carboxyl groups in the usual manner, for example by reaction with ammonia or a primary or secondary amine and, if necessary, dehydration of the ammonium salt formed as an intermediate.

Free carboxyl groups can, for example, also be converted into acid halide or acid anhydride groups in the usual manner, for example by reaction with halides of phosphorus or sulphur, such as thionyl chloride, phosphorus pentachloride or phosphorus tribromide, or with acid halides, such as chloroformic acid esters or oxalyl chloride. The acid anhydride or acid halide groups can then be converted into esterified carboxyl groups in the usual manner by reaction with corresponding alcohols, if desired, in the presence of acid-binding agents, such as organic or inorganic bases.

Functionally modified carboxyl groups as a constituent of $R_2$ can furthermore be converted into esterified or amidised carboxyl groups according to customary methods. Thus, resulting acid anhydrides, such as acid halides, for example acid chlorides, or ketenes can be converted into esters or amides by reaction with, respectively, an alcohol or ammonia or a primary or secondary amine, if desired in the presence of acid-binding agents, such as organic or inorganic bases. Resulting nitriles can also be converted analogously, by reaction with an alcohol into the corresponding iminoethers which can be hydrolysed in the usual manner to the corresponding esters.

The reactions mentioned can optionally be carried out simultaneously or successively and in any desired sequence.

The reactions mentioned are carried out in the usual manner in the presence or absence of diluents, condensation agents and/or catalytic agents, at lowered, ordinary or elevated temperature, if appropriate in a closed vessel.

Depending on the process conditions and starting materials, the end products are obtained in the free form or in the form of their acid addition salts which is also encompassed by the invention. Thus, for example, basic, neutral or mixed salts and possibly also hemihydrates, monohydrates, sesquihydrates or polyhydrates thereof can be obtained. The acid addition salts of the new compounds can be converted into the free compound in a manner which is in itself known, for example by means of basic agents, such as alkalis or ion exchangers. On the other hand, the resulting free bases can form salts with organic or inorganic acids. Acids used for the manufacture of acid addition salts are especially those which are suitable for forming therapeutically usable salts. As examples of such acids there may be mentioned: Hydrogen halide acids, sulphuric acids, phosphoric acids, nitric acids, perchloric acid, aliphatic, alicyclic, aromatic or heterocyclic carboxylic acids or sulphonic acids, such as formic acid, acetic acid, propionic acid, succinic acid, glycollic acid, lactic acid, malic acid, tartaric acid, citric acid, ascorbic acid, maleic acid, hydroxymaleic acid or pyruvic acid, fumaric acid, benzoic acid, anthranilic acid, p-hydroxybenzoic acid or salicyclic acid, embonic acid, methanesulphonic acid, ethanesulphonic acid, cyclohexanesulphonic acid, hydroxyethanesulphonic acid and ethylenesulphonic acid, halogenobenzenesulphonic acids, toluenesulphonic acid, naphthalenesulphonic acid or sulphanilic acid, methionine, tryptophane, lysine or arginine.

Acid compounds can furthermore be in the free form or in the form of their salts with bases, such as alkali metal salts or alkaline earth metal salts, salts with ammonia or salts with amines. Suitable compounds for the manufacture of salts with bases are, for example, alkali metal, such as sodium or potassium, carbonates, bicarbonates or hydroxides, or corresponding alkaline earth metal compounds, such as calcium or magnesium compounds, or ammonia, as well as amines, such as aliphatic amines, for example lower alkylamines, such as trimethylamine or triethylamine. Aluminium salts, for example salts of two mols of acid and one mol of aluminium hydroxide, are also suitable, especially because of their slower resorption, absence of odour and the fact that they cause little gastro-intestinal disturbance.

There or other salts of the new compounds such as, for example, the picrates, can also be used to purify the resulting free bases, by converting the free compound into salts, isolating these and again liberating the compound from the salts. Because of the close relationships between the new compounds in the free form and in the form of their salts, the free compounds are, in the preceding and following text, where appropriate also to be understood to include the corresponding salts, with regard to general sense and intended use.

The invention also relates to those embodiments of the process according to which a compound obtainable as an intermediate product at any stage of the process is used as the starting material and the missing process steps are carried out, or the process is discontinued at any stage, or in which a starting material is formed under the reaction conditions or in which a reactant is in the form of its salts, if relevant.

Thus, a possible procedure is to react an aldehyde of the formula XI

Py—Ph—O—CH$_2$—CHOH—CHO  (XI)

with an amine HNR$_1$R$_2$, wherein Py, Ph, R$_1$ and R$_2$ have the above meanings, in the presence of a suitable reducing agent, such as one of those mentioned above. In this case, a compound of the formula VIIa or VIIb is used as an intermediate product and is then reduced in accordance with the invention.

A further suitable procedure is to react an amine of the formula XII

Py—Ph—O—CH$_2$—CHOH—CH$_2$—NH$_2$ (XII)

with an aldehyde or ketone of the formula O=R$_2$, wherein Py, Ph and R$_2$ have the above meaning, in the presence of a suitable reducing agent, such as one of those mentioned above. This gives, as the intermediate product, a compound of the formula VIIIa or VIIIb or IXa or IXb, which is then reduced in accordance with the invention.

A further suitable procedure is to heat a compound of the formula X with an $\alpha,\beta,\gamma,\delta$-tetrahydroxy-$\epsilon$-carboxy-lower alkanecarboxylic acid, such as music acid or saccharic acid, with elimination of carbon dioxide and water. Hereupon, a $\gamma$-oxo-lower alkanone or a tautomer thereof is obtained as an intermediate product and then reacts further according to the invention. The heating is preferably carried out to between +100° and +300° in the presence or absence of inert organic solvents of medium or fairly high boiling point or boiling range such as, for example, xylenes, xylene mixtures or diethylene glycol dimethyl ether. The reaction to give a compound I can also proceed through the decarboxylation partially only occurring after the cyclisation to the pyrrole has taken place, so that after the reaction has taken place any carboxyl groups still present are finally split off as carbon dioxide by stronger heating. It is also advantageously possible to convert a mucic acid or saccharic acid salt of a compound X into compounds I by dry distillation or sublimation, the pressure being reduced, if appropriate, in such a way as to give a favourable reaction temperature.

Depending on the choice of the starting materials and procedures, the new compounds can be in the form of optical antipodes or racemates, or, if they contain at least two asymmetric carbon atoms, also as racemate mixtures and/or as pure geometrical isomers or as mixtures thereof (isomer mixtures).

Resulting isomer mixtures can be separated into the two pure geometrical isomers in a known manner on the basis of the physico-chemical differences of the constituents, for example by chromatography on a suitable stationary phase, such as silica gel, or aluminium oxide, which have been pretreated with a complex-forming heavy metal compound, for example with a silver compound, or by forming a heavy metal addition compound, for example the silver nitrate complex, separating this into the addition compounds of the pure isomers, for example by fractional crystallisation and subsequently liberating the pure isomers.

Racemate mixtures can be separated into the two stereoisomeric (diastereomeric) pure racemates in a known manner on the basis of the physico-chemical differences of the constituents, for example by chromatography and/or fractional crystallisation.

Resulting racemates can be separated into the diastereomers according to known methods, for example by recrystallisation from an optically active solvent, with the aid of micro-organisms or by reaction with an optically active acid which forms salts with the racemic compound and separation of the salts obtained in this manner, for example on the basis of their different solubilities, and the antipodes can be liberated from the diastereomers by the action of suitable agents. Particularly customary optically active acids are, for example, the D- and L-forms of tartaric acid, di-o-toluyltartaric acid, malic acid, mandelic acid, camphorsulphonic acid or quinic acid. Advantageously, the more active L-antipode is isolated.

Appropriately, the starting materials used for carrying out the reactions according to the invention are those which lead to the initially particularly mentioned groups of end products and especially to the end products which have been particularly described or singled out.

The starting materials are known or can, if they are new, be obtained according to methods which are in themselves known.

Compounds of the formula II can be manufactured, for example, in the usual manner, from a phenol Py-Ph-OH or a phenolate thereof, by means of epichlorohydrin or the like. Compounds of the formula V can be manufactured, for example, in the usual manner from an amine HNR$_1$R$_2$ and epichlorohydrin or the like. Compounds of the formula I with removable radicals on the amino group and/or hydroxyl group can, for example, be manufactured in the usual manner from a phenol Py-Ph-OH or a phenolate thereof and an appropriately substituted compound of the formula V. Compounds of the formula X can be manufactured, for example, in the usual manner from a phenol H$_2$H-Ph-PH or a phenolate thereof, by means of a compound of the formula V. Compounds of the formula XI can be manufactured, for example, in the usual manner from a phenol Py-Ph-OH or a phenolate thereof and 2,3-epoxy-propionaldehyde. Compounds of the formula XII can be manufactured, for example, in the usual manner from a phenol Py-Ph-OH or a phenolate thereof and 2,3-epoxy-n-propylamine.

The new compounds can be used as medicaments, for example in the form of pharmaceutical preparations, in which they or their salts are present as a mixture with a pharmaceutical, organic or inorganic, solid or liquid excipient suitable for enteral or parenteral administration. Suitable materials for forming the excipient are those which do not react with the new compounds such as, for example, water, gelatine, lactose, starch, magnesium stearate, talc, vegetable oils, benzyl alcohols, rubber, polyalkylene glycols, white petroleum jelly, cholesterol or other known medicinal excipients. The pharmaceutical preparations can be, for example, in the form of tablets, dragees, capsules or suppositories or in a liquid form, as solutions (for example as an elixir or syrup), suspension or emulsions. They are optionally sterilised and/or contain auxiliaries, such as preservatives, stabilisers, wetting agents or emulsifiers, salts for regulating the osmotic pressure or buffers. They can also contain yet other therapeutically valuable materials. The preparations, which can also be used in veterinary medicine, are formulated according to customary methods.

The examples which follow illustrate the invention without, however, restricting it.

EXAMPLE 1

10 g(0.047 mol) of 1-[4-pyrrolyl-(1)-phenoxy]-2,3-epoxy-propane are dissolved in 100 ml of isopropanol, 4.25 ml (0.05 mol) of isopropylamine are added and the mixture is then heated to the boil for 3 hours under reflux. It is then evaporated in vacuo and the resulting crude base is crystallised from ethyl acetate. 1-[4-Pyrrolyl-(1)-phenoxy]-2-hydroxy-3-isopropylamino-propane is obtained, of which the hydrochloride, prepared from a solution of the base in methanol and a solution of hydrogen chloride in ether, melts at 208°–210° C.

The starting material can be prepared as follows:

5.0 g (31.4 mmols) of 4-pyrrolyl-(1)-phenol, 11.6 g (9.9 ml) of epichlorohydrin and 0.1 ml of piperidine are heated for 6 hours under reflux. Instead of the piperidine, a small amount of potassium carbonate and acetonitrile can also be used. The excess epichlorohydrin is then distilled off and the residue is distilled at 160° C and 0.05 mm Hg. The resulting 1-[4-pyrrolyl-(1)-phenoxy]-2,3-epoxy-propane can be used further direct. The 4-pyrrolyl-(1)-phenol used can, in turn, be obtained from p-aminophenol and 2,5-dimethoxy-tetrahydrofurane in glacial acetic acid.

EXAMPLE 2

40 g (0.18 mol) of 1-(4-amino-phenoxy)-2-hydroxy-3-isopropylamino-propane and 25 g (0.189 mol) of 2,5-dimethoxy-tetrahydrofurane in 400 ml of glacial acetic acid are heated for 1 1/2 hours under reflux. The acetic acid is distilled off under reduced pressure. The residue is dissolved in ethyl acetate and the solution is washed twice with sodium hydroxide solution and twice with water. The ethyl acetate phase is dried over magnesium sulphate, filtered and concentrated until crystallisation starts. 1-[4-Pyrrolyl-(1)-phenoxy]-2-hydroxy-3-isopropylaminopropane is obtained.

The hydrochloride is obtained from the base by reacting a solution of the base in methanol with a solution of hydrogen chloride in ether. The hydrochloride melts at 208°–210° C.

EXAMPLE 3

108 g (0.482 mol) of 1-(2-amino-phenoxy)-2-hydroxy-3-isopropylamino-propane and 64 g (0.482 mol) of 2,5-dimethoxy-tetrahydrofurane in 1,080 ml of glacial acetic acid are heated for 1 hour under reflux. The glacial acetic acid is distilled off under reduced pressure. The residue is partitioned between ethyl acetate and sodium hydroxide solution. The ethyl acetate phase is washed once with sodium hydroxide solution and twice with water, dried over magnesium sulphate, filtered and concentrated. The residue obtained is a dark brown oil which is taken up in ether and the ether solution is filtered. The filtrate is evaporated under reduced pressure. The residue is again dissolved in ether, the solution is filtered and the filtrate is evaporated under reduced pressure. Light yellow crystals are thus obtained, which are recrystallised from ether/petroleum ether and consist of 1-[2-pyrrolyl-(1)-phenoxy]-2-hydroxy-3-isopropylamino-propane, melting point 80°–81° C. With hydrogen chloride in methanol, the hydrochloride is obtained, which after recrystallisation from isopropanol melts at (129° C) 130°–131° C.

The starting material can be prepared as follows:

290 g (1.14 mol) of 1-(2-nitro-phenoxy)-2-hydroxy-3-isopropylamino-propane are dissolved in 1.5 l of ethanol.

280 ml (5.7 mols) of hydrazine hydrate are added to the solution. About 100 ml of this solution are introduced into a flask and warmed to about 70° C. Raney nickel is then added in portions. The remainder of the solution is then allowed to run in in such a way that the temperature is kept at about 70° C (reflux) by the heat of reaction. After completion of the addition, the mixture is stirred for a further hour and is filtered after it has cooled. The filtrate is concentrated until it crystallises and 1-(2-amino-phenoxy)-2-hydroxy-3-isopropylamino-propane of melting point 94°–97° C is thus obtained.

EXAMPLE 4

Tablets containing 60 mg of active substance are prepared in the usual manner, to have the following composition:

| Composition | |
|---|---|
| 1-[4-Pyrrolyl-(1)-phenoxy]-2-hydroxy-3-isopropylamino-propane hydrochloride | 60 mg |
| Wheat starch | 59 mg |
| Lactose | 60 mg |
| Colloidal silica | 10 mg |
| Talc | 10 mg |
| Magnesium stearate | 1 mg |
| | 200 mg |

Preparation

The 1-[4-pyrrolyl-(1)-phenoxy]-2-hydroxy-3-isopropylamino-propane hydrochloride is mixed with a part of the wheat starch, with lactose and with colloidal silica and the mixture is forced through a sieve. A further part of the wheat starch is worked into a paste with a 5-fold amount of water on a waterbath and the powder mixture is kneaded with this paste until a slightly plastic mass has been produced.

This plastic mass is forced through a sieve of approx. 3 mm mesh width and dried, and the resulting dry granules are again forced through a sieve. The remaining wheat starch, talc and mangesium stearate are then mixed in and the mixture is pressed to give tablets weighing 200 mg and having a breaking groove. The daily dose is about 1/2 to 4 tablets in the case of a warm-blooded animal of about 75 kg body weight, it also being possible to administer the corresponding dose of active compound as a single tablet of appropriate composition.

Tablets containing 60 mg of 1-[2-pyrrolyl-(1)-phenoxy]-2-hydroxy-3-isopropyl-amino-propane hydrochloride as the active compound can be prepared analogously.

EXAMPLE 5

52 ml of tert.butylamine are added to a solution of 26.9 g of 1-[o-(pyrrol-1-yl]-2,3-epoxy-propane in 250 ml of isopropanol and the mixture is heated to the boil under reflux for 1½ hours. The oil which remains after evaporating off the volatile constituents in vacuo is distilled in a high vacuum in a bulb tube and gives 1-tert.butylamino3-[o-(pyrrol-1-yl)-phenoxy]-2-propanol as a colourless oil of boiling point 130°–140° C/0.04 mm Hg. With half the equivalent amount of fumaric acid, this forms a neutral fumarate of melting point 203°–204° C (from methanol).

The starting material can be prepared as follows:

a. 109 g of o-aminophenol and 132 g of 2,5-dimethoxy-tetrahydrofurane in 700 ml of glacial acetic acid are heated to the boil for 30 minutes. After cooling, the reaction mixture is filtered and the polymeric material is thus removed. The filtrate is evaporated in vacuo, the residue is dissolved in approx. 1 liter of ethyl acetate and the solution is washed with 200 ml of water. The dark oil which remains after drying and evaporating the organic phase is distilled in a bulb tube under a high vacuum. This gives o-(pyrrol-1-yl)-phenol of boiling point 115°–125° C/0.05 mm Hg as an oil which gradually crystallises and melts at 46°–49° C.

b. 95.7 g of o-(pyrrol-1-yl)-phenol, 245 g of potassium carbonate and 167 g of epichlorohydrin are heated to the boil in a nitrogen atmosphere, whilst stirring. After 6 hours, the reaction mixture is cooled and filtered and the filtrate is evaporated in vacuo, ultimately at a bath temperature of 120° C. The oil which remains is dissolved in 300 ml of ether and the solution is extracted with 300 ml of 2 N sodium hydroxide solution and washed with 100 ml of water. The oil which remains after evaporating off the solvent is distilled in a high vacuum and gives 1-[o-(pyrrol-1-yl)-phenoxy]-2,3-epoxy-propane of boiling point 103°–105° C/0.001 mm Hg.

EXAMPLE 6

50 ml of isopropylamine are added to a solution of 26.9 g of 1-[o-(pyrrol-1-yl)-phenoxy]-2,3-epoxy-propane in 250 ml of isopropanol and the mixture is heated to the boil under reflux for 1 1/2 hours. The oil which remains after evaporating off the volatile constituents in vacuo is distilled in a bulb tube under a high vacuum and gives 1-iso-propylamino-3[o-(pyrrol-1-yl)-phenoxy]-2-propanol as a colourless oil of boiling point 125°–135° C/0.04 mm Hg. The distillate which crystallises can be recrystallised from ether/petroleum ether and gives crystals of melting point 80°–81° C and is in every respect identical with the product obtained in Example 3.

EXAMPLE 7

A solution of 15 g of 1-[o-(pyrrol-1-yl)-phenoxy]-2,3-epoxy-propane and 7 g of morpholine in 150 ml of isopropanol is heated for 2 hours to the boil under reflux. After evaporation in vacuo, an oil remains, which crystallises and after recrystallisation from butanone gives 1-morpholino-3-[o-(pyrrol-1-yl)-phenoxy]-2-propanol of melting point 81°–82° C. It forms a neutral fumarate of melting point 136°–137° C (from butanone).

EXAMPLE 8

30 g of 1-[o-(2,5-dimethyl-pyrrol-1-yl)-phenoxy]-2,3-epoxy-propane, dissolved in 200 ml of isopropanol, are mixed with 60 ml of isopropylamine and the mixture is heated to the boil under reflux for 2 hours. The oil which remains after evaporation is recrystallised from petroleum ether with addition of active charcoal and gives 1-[o-(2,5-dimethyl-pyrrol-1-yl)-phenoxy]-3-isopropylamino2-propanol of melting point 73°–75° C. Its neutral fumarate melts at 186°–188° C (from acetone).

The starting materials required can be prepared analogously to Example 5:

a. o-Aminophenol and 2,5-hexanedione give o-(2,5-dimethyl-pyrrol-1-yl)-phenol of melting point 95°–99° C.

b. o-(2,5-Dimethyl-pyrrol-1-yl)-phenol and epichlorohydrin give 1-[o-(2,5-dimethyl-pyrrol-1-yl)-phenoxy]-2,3-epoxy-propane of boiling point 120°–122° C/0.08 mm Hg.

What we claim is:

1. A pharmaceutical composition useful as blockers of adrenergic β-receptors in the treatment of heart and circulatory ailments comprising a therapeutically effective amount of a pyrrolyl compound of the formula I

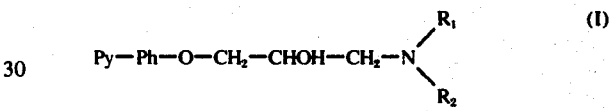

wherein Py is 1-pyrrolyl or mono- or di-lower alkylated 1pyrrolyl, Ph is phenylene, $R_1$ is hydrogen or lower alkyl and $R_2$ is hydrogen, lower alkyl, phenyl-lower alkyl having up to 10 carbon atoms wherein the phenyl ring is unsubstituted or monosubstituted by lower alkyl, lower alkoxy, halogen or trifluoromethyl, or $R_1$ and $R_2$ together are lower alkylene, their antipodes or salts, together with a pharmaceutical excipient.

2. A method for the treatment of heart and circulatory ailments in a warm-blooded animal which comprises the administration thereto of a therapeutically effective amount of a compound of formula I defined in claim 1.

* * * * *